(12) United States Patent
Kubota

(10) Patent No.: US 10,820,891 B2
(45) Date of Patent: Nov. 3, 2020

(54) ULTRASONIC PROBE AND ULTRASONIC DIAGNOSTIC APPARATUS

(71) Applicant: TOSHIBA MEDICAL SYSTEMS CORPORATION, Otawara (JP)

(72) Inventor: Takashi Kubota, Otawara (JP)

(73) Assignee: Canon Medical Systems Corporation, Otawara (JP)

( * ) Notice: Subject to any disclaimer, the term of this patent is extended or adjusted under 35 U.S.C. 154(b) by 1078 days.

(21) Appl. No.: 15/044,580

(22) Filed: Feb. 16, 2016

(65) Prior Publication Data

US 2016/0338675 A1 Nov. 24, 2016

(30) Foreign Application Priority Data

May 18, 2015 (JP) ................. 2015-100895

(51) Int. Cl.
*A61B 8/00* (2006.01)
*A61B 8/12* (2006.01)
(Continued)

(52) U.S. Cl.
CPC ............ *A61B 8/54* (2013.01); *A61B 8/085* (2013.01); *A61B 8/0841* (2013.01); *A61B 8/12* (2013.01); *A61B 8/4254* (2013.01); *A61B 8/4461* (2013.01); *A61B 8/4477* (2013.01); *A61B 8/4494* (2013.01); *A61B 8/461* (2013.01);
(Continued)

(58) Field of Classification Search
CPC ......... A61B 8/54; A61B 8/0841; A61B 8/085; A61B 8/12; A61B 8/4254; A61B 8/4461; A61B 8/4477; A61B 8/4494; A61B 8/461; A61B 90/11; A61B 17/3403; G01N 29/26; G01S 15/892; G01S 15/8919; G01S 15/894; G01S 15/8945

See application file for complete search history.

(56) References Cited

U.S. PATENT DOCUMENTS 4,869,258 A * 9/1989 Hetz .................... A61B 8/0841
600/446
5,720,287 A * 2/1998 Chapelon ................. A61B 8/12
600/439
(Continued)

FOREIGN PATENT DOCUMENTS

JP 2-36854 2/1990
JP 2-91512 U 7/1990
(Continued)

OTHER PUBLICATIONS

Translation of Yamamoto (Year: 2007).*
Japanese Office Action dated Mar. 19, 2019 in Patent Application No. 2015-100895, 4 pages.

*Primary Examiner* — Carolyn A Pehlke
(74) *Attorney, Agent, or Firm* — Oblon, McClelland, Maier & Neustadt, L.L.P.

(57) ABSTRACT

The ultrasonic probe according to the present embodiment includes a first transducer set, a second transducer set and a transducer set supporter. The first transducer set arranges transducers in a direction parallel with an axis of the ultrasonic probe. The second transducer set arranges transducers on a plane substantially orthogonal to the axis. The transducer set supporter supports the first transducer set and the second transducer set, and is configured to pivot around the axis.

16 Claims, 16 Drawing Sheets

(51) Int. Cl.
- *A61B 8/08* (2006.01)
- *G01S 15/89* (2006.01)
- *G01N 29/265* (2006.01)
- *A61B 90/11* (2016.01)
- *A61B 17/34* (2006.01)
- *A61B 90/00* (2016.01)
- *G10K 11/34* (2006.01)
- *G01S 7/52* (2006.01)
- *G10K 11/35* (2006.01)
- *B06B 1/06* (2006.01)

(52) U.S. Cl.
CPC .......... *A61B 17/3403* (2013.01); *A61B 90/11* (2016.02); *G01N 29/265* (2013.01); *G01S 15/892* (2013.01); *G01S 15/894* (2013.01); *G01S 15/8918* (2013.01); *G01S 15/8945* (2013.01); *A61B 2090/067* (2016.02); *A61B 2090/378* (2016.02); *B06B 1/0659* (2013.01); *G01N 2291/105* (2013.01); *G01N 2291/106* (2013.01); *G01S 7/52073* (2013.01); *G10K 11/346* (2013.01); *G10K 11/352* (2013.01)

(56) References Cited

U.S. PATENT DOCUMENTS

| | | | | |
|---|---|---|---|---|
| 5,876,345 | A | * | 3/1999 | Eaton ................ A61B 8/12 600/463 |
| 6,045,508 | A | | 4/2000 | Hossack et al. |
| 8,727,986 | B2 | * | 5/2014 | Hall ................ A61B 5/435 600/438 |

FOREIGN PATENT DOCUMENTS

| | | |
|---|---|---|
| JP | 3-182237 A | 8/1991 |
| JP | 2006-320590 A | 11/2006 |
| JP | 2007020837 A * | 2/2007 |

* cited by examiner

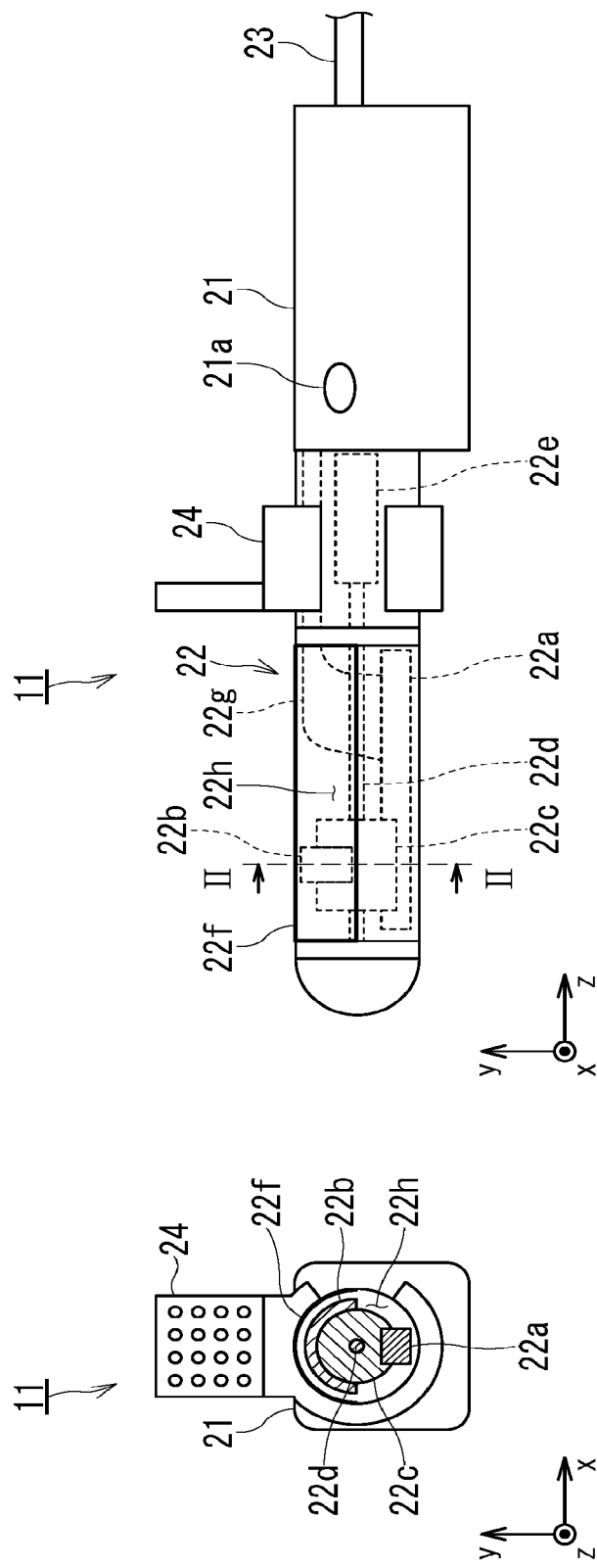
F I G. 3

ULTRASONIC PROBE AND ULTRASONIC DIAGNOSTIC APPARATUS

CROSS-REFERENCE TO RELATED APPLICATION

This application is based upon and claims the benefit of priority from Japanese Patent Application No. 2015-100895, filed on May 18, 2015, the entire contents of which are incorporated herein by reference.

FIELD

Embodiments as an aspect of the present invention relate to an ultrasonic probe and an ultrasonic diagnostic apparatus.

BACKGROUND

In the field of medical applications, ultrasonic diagnostic apparatuses have been used which utilize ultrasound generated by using transducers (piezoelectric devices) of an ultrasonic probe to perform imaging of the interior of an object. An ultrasonic diagnostic apparatus transmits ultrasound into an object from an ultrasonic probe connected to the ultrasonic diagnostic apparatus, and receives reflected waves, which are caused by inconsistencies of acoustic impedance in the interior of the object, with an ultrasonic probe. The ultrasonic diagnostic apparatus creates a received signal based on a reflected wave received at the ultrasonic probe, and obtains a desired ultrasonic image through image processing.

As a prior art for the structure of ultrasonic probe, there has been disclosed an ultrasonic probe for use inside a body cavity, which includes a first transducer set in which transducers are arranged on an outer peripheral surface of the probe body so as to be parallel with the axis of the probe, and a second transducer set in which transducers are arranged along a direction orthogonal to the axis of the probe.

According to the prior art ultrasonic probe, change-over between the first transducer set and the second transducer set is performed by manually rotating the ultrasonic probe around its axis. Therefore, such a rotating operation during manipulation is a burden for the operator.

Moreover, it is difficult to perform the rotating operation so as to cause a puncture target, which has appeared on a scanning plane by either of the transducer sets, to appear on a scanning plane by another of the transducer sets after change-over.

Further, when a puncture adaptor for guiding a puncture needle has be attached to the ultrasonic probe, a rotation support mechanism is provided in the ultrasonic probe and the puncture adaptor to make the ultrasonic probe rotatable while holding the position of the puncture adaptor. As a result, due to the effect of operations such as rotating of the ultrasonic probe, the operation to hold the puncture adaptor so as to prevent fluctuation of its position becomes a burden for the operator.

Accordingly, it is an objective of the present invention to provide an ultrasonic probe and an ultrasonic diagnosis apparatus, which can improve operability by the operator.

BRIEF DESCRIPTION OF THE DRAWINGS

In accompanying drawings,

FIG. 3 is a diagram showing a second example structure of the ultrasonic probe according to the first embodiment;

DETAILED DESCRIPTION

An ultrasonic probe and an ultrasonic diagnostic apparatus according to the present embodiment will be described with reference to the appended drawings.

The ultrasonic probe according to the present embodiment includes a first transducer set, a second transducer set and a transducer set supporter. The first transducer set arranges transducers in a direction parallel with an axis of the ultrasonic probe. The second transducer set arranges transducers on a plane substantially orthogonal to the axis. The transducer set supporter supports the first transducer set and the second transducer set, and is configured to pivot around the axis.

First Embodiment

Figure 1:
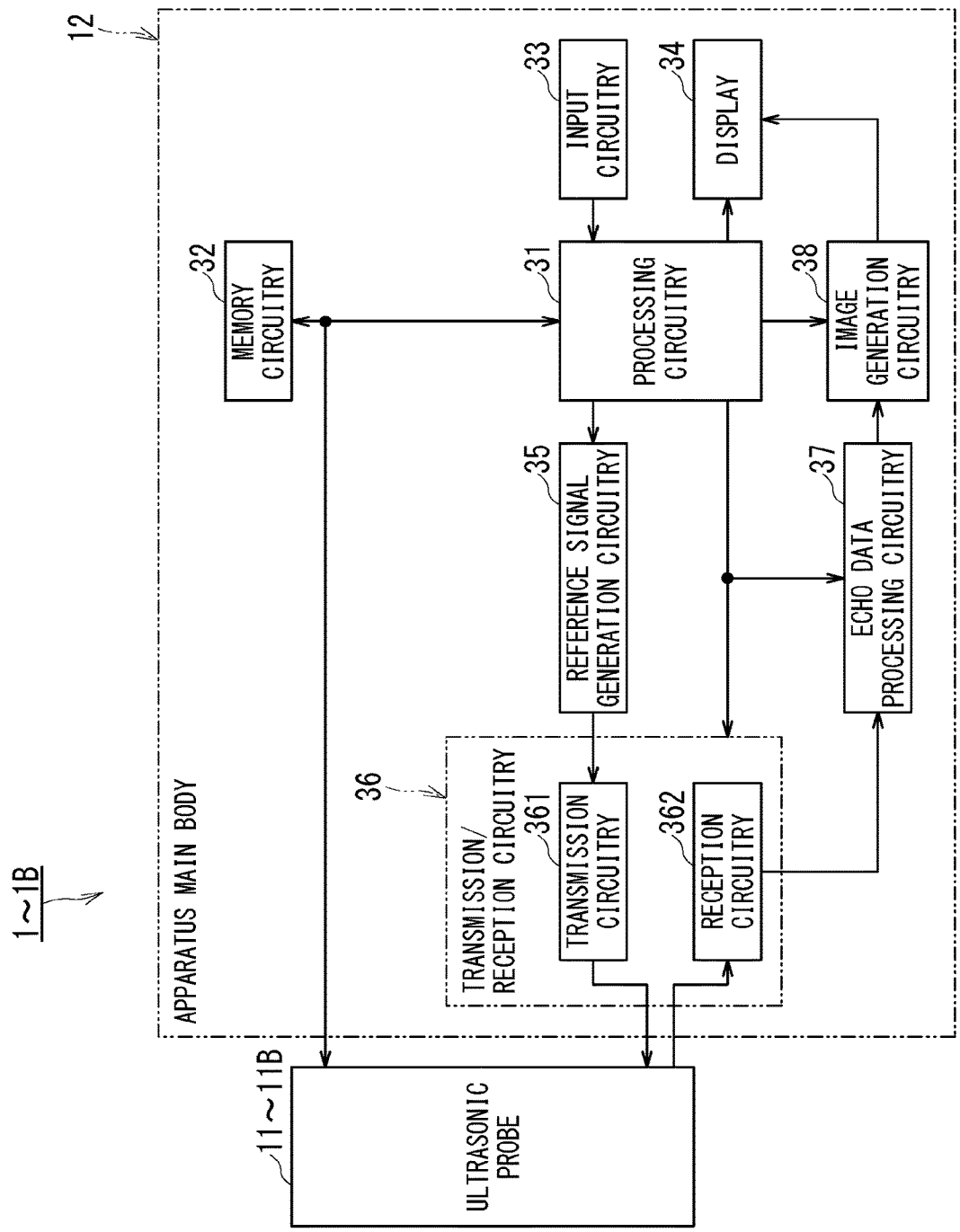
FIG. 1 is a schematic diagram showing a configuration of an ultrasonic probe and an ultrasonic diagnostic apparatus according to a first embodiment.

FIG. 1 is a schematic diagram showing a configuration of an ultrasonic probe and an ultrasonic diagnostic apparatus according to a first embodiment.

FIG. 1 shows an ultrasonic diagnostic apparatus 1 according to the first embodiment, and an ultrasonic probe 11 according to the first embodiment and an apparatus main body 12, which are included in the ultrasonic diagnostic apparatus 1.

The ultrasonic probe 11 is one principally for use inside a body cavity, which is suitable for being inserted through the rectum to image an internal organ. The ultrasonic probe 11 performs transmission/reception of ultrasound to and from an object according to control by the apparatus main body 12.

Figure 2:
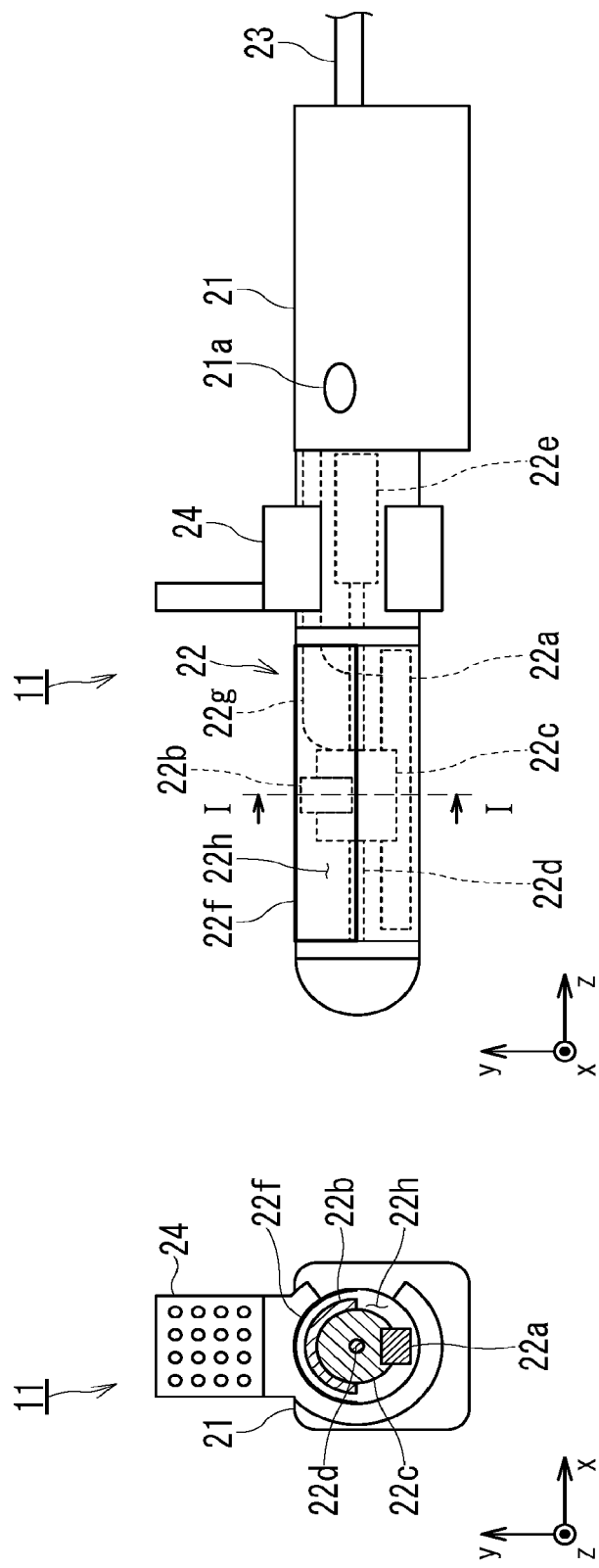
FIG. 2 is a diagram showing a first example structure of the ultrasonic probe according to the first embodiment.

FIG. 2 is a diagram showing a first example structure of the ultrasonic probe 11 according to the first embodiment.

Shown on the left-hand side of FIG. 2 is a I-I section (x-y section) of the ultrasonic probe 11 shown on the right-hand side of FIG. 2, and shown on the right-hand side of FIG. 2 is a side view (viewed from a y-z plane) of the ultrasonic probe 11.

The ultrasonic probe 11 includes a handle portion 21, a probe body (distal end portion) 22, and a cable 23. The handle portion 21 includes a changing-over switch 21a for instructing changing-over of a scanning, that is, pivoting of a pivot shaft 22d to be described later. The pivoting of the pivot shaft 22d includes pivoting in positive direction and pivoting in negative direction. Note that the ultrasonic probe 11 may include a scale visually perceptible by the operator, which indicates a pivoting angle of the pivot shaft 22d to be described later.

Further, the ultrasonic probe 11 may be equipped with a puncture adaptor 24 for guiding a puncture needle. Through holes for guiding a puncture needle are formed at predetermined positions of the puncture adaptor 24.

The probe body 22 includes a first transducer set 22a, a second transducer set 22b, a transducer set supporter 22c, a pivot shaft (pivot unit) 22d, a pivot driver (motor) 22e, an acoustic window 22f, a signal line 22g, and a solution layer 22h. It is supposed that scanning types by the first transducer set 22a and by the second transducer set 22b are different from each other.

A center position in a direction (z direction) parallel with an axis of the probe body 22, of the second transducer set 22b of the ultrasonic probe 11 substantially corresponds to a center position in the z direction, of the first transducer set 22a. Moreover, in an orthogonal plane (x-y section) with respect to the z direction, an angle α (shown in FIG. 7) formed between a scanning plane of the first transducer set 22a and a center line of the second transducer set 22b is preferably a straight angle (180°). This is because the puncture needle advances in parallel with the z direction when the ultrasonic probe 11 is used.

The first transducer set 22a has a structure in which transducers (piezoelectric devices) are arranged in a row along the z direction. The row along the z direction may be one or more rows. Each transducer is an electro-acoustic transducer, which has a function of converting an electric pulse into an ultrasonic pulse (transmission ultrasound) during transmission, and converting an ultrasonic reflected wave (reception ultrasound) into an electric signal (received signal) during reception. The first transducer set 22a is, for example, a linear array. Hereafter, description will be made by taking as an example a case in which the first transducer set 22a is a linear array.

When the transducers are arranged in 1 to about 3 rows in the linear array 22a, a lens member (not shown) for focusing ultrasound in the arrangement direction (x direction) is provided in a front side of the linear array 22a. On the other hand, when the transducers are arranged in a sufficient number of rows in the linear array 22a, electronic focusing is used to focus ultrasound in the x direction.

The second transducer set 22b has a structure in which transducers are arranged on a plane (x-y section) substantially orthogonal to the z direction. The second transducer set 22b includes the transducers arranged on the one plane substantially orthogonal to the z direction or on multiple planes substantially orthogonal to the z direction. The second transducer set 22b is, for example, a convex array in which the transducers are arranged on a plane substantially orthogonal to the z direction, and in a portion of a circumference whose radius of curvature substantially corresponds to a pivoting radius. Hereafter, description will be made taking as an example a case in which the second transducer set 22b is a convex array.

When the transducers are arranged in 1 to about 3 planes in the convex array 22b, a lens member (not shown) for focusing ultrasound in the z direction is provided in a front side of the convex array 22b. On the other hand, when the transducers are arranged in a sufficient number of planes in the convex array 22b, electronic focusing is used to focus ultrasound in the z direction.

Note that although it is supposed that a bucking for preventing back reflection is provided in a rear side of each of the arrays 22a and 22b, description thereof will be omitted.

The transducer set supporter 22c supports the arrays 22a and 22b such that the angle formed between the scanning plane of the linear array 22a and the center line of the convex array 22b is kept at constant in the x-y section.

The pivot shaft 22d supports the transducer set supporter 22c (arrays 22a and 22b) and pivots around an axis of the probe body 22 through the pivot driver 22e. That is, the pivot shaft 22d is provided on the axis of the probe body 22.

The pivot driver 22e drives the pivot shaft 22d to pivot itself according to a pivoting angle instructed from the apparatus main body 12 upon depression of the changing-over switch 21a. Note that, upon depression of the changing-over switch 21a, the pivot driver 22e may drive the pivot shaft 22d to pivot itself according to a previously set, fixed pivoting angle.

The acoustic window 22f is provided in the whole or a part (a portion of transmission/reception opening) of the circumference around the axis of the probe body 22 out of the housing, which is in contact with the object, and is made of a material which easily transmits ultrasound. The housing, whose axial center substantially corresponds to the pivot shaft 22d (pivoting center), accommodates the linear array 22a, the convex array 22b, the transducer set supporter 22c, the pivot shaft 22d, the pivot driver 22e, and a part of the signal line 22g.

The signal line 22g is connected to each transducer of the arrays 22a and 22b. While the signal line 22g is drawn out to the cable 23, for example, through inside a bucking (not shown), illustration and description of the drawn out signal lines 22g and a substrate to which the signal line 22g is connected will be omitted.

The solution layer 22h is provided inside the probe body 22, and is a layer filled with a liquid or fluid matter (sound medium) which easily transmits an ultrasonic signal.

The cable 23 connects the probe body 22 with transmission circuitry 361 and reception circuitry 362 of transmission/reception circuitry 36.

FIG. 3 is a diagram showing a second example structure of the ultrasonic probe 11 according to the first embodiment.

Shown on the left-hand side of FIG. 3 is a II-II section (x-y section) of the ultrasonic probe 11 shown on the right-hand side of FIG. 3, and shown on the right-hand side of FIG. 3 is a side view (viewed from a y-z plane) of the ultrasonic probe 11.

The ultrasonic probe 11 shown in FIG. 3 has a structure in which the center position in the z direction, of the convex array 22b is deviated toward a distal end side than the center position in the z direction, of the linear array 22a.

According to the ultrasonic probe 11 shown in FIG. 3, it is possible to effectively support operator's manipulation to advance a puncture needle to an organ, such as the prostate while confirming an ultrasonic image by a convex scanning using the convex array 22b. Therefore, according to the ultrasonic probe 11 shown in FIG. 3, it is possible to improve the accuracy of insertion into the prostate.

Moreover, since the distance from the convex array 22b to the distal end of the ultrasonic probe 11 can be made relatively short, it is possible to reduce the amount of insertion of the ultrasonic probe 11 into an object.

Figure 4:
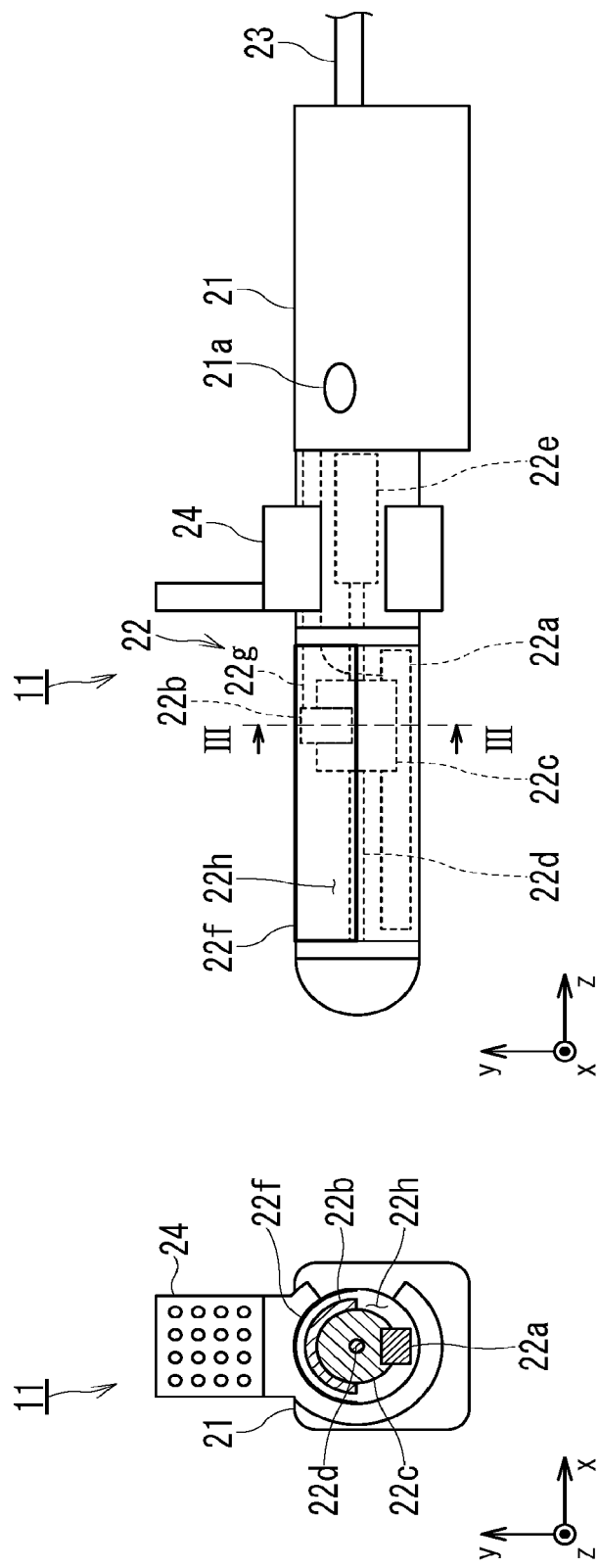
FIG. 4 is a diagram showing a third example structure of the ultrasonic probe according to the first embodiment.

FIG. 4 is a diagram showing a third example structure of the ultrasonic probe 11 according to the first embodiment.

Shown on the left-hand side of FIG. 4 is a section (x-y section) of the ultrasonic probe 11 shown on the right-hand side of FIG. 4, and shown on the right-hand side of FIG. 4 is a side view (viewed from a y-z plane) of the ultrasonic probe 11.

The ultrasonic probe 11 shown in FIG. 4 has a structure in which the center position in the z direction, of the convex array 22b is deviated toward the handle portion 21 side than the center position in the z direction, of the linear array 22a.

According to the ultrasonic probe 11 shown in FIG. 4, the distance between the convex array 22b and the puncture adaptor 24 can be made short. Therefore, according to the ultrasonic probe 11 shown in FIG. 4, it is possible to improve the accuracy of puncturing into a puncture target when the puncture target is located in a shallow position in the object.

Note that the ultrasonic probe 11 may have a structure in which the convex array 22b is slidable in the z direction with respect to the linear array 22a. In that case, the arrangements of the convex array 22b shown in FIGS. 2 to 4 can be freely selected.

Referring back to description of FIG. 1, the apparatus main body 12 includes processing circuitry 31, memory circuitry (storage unit) 32, input circuitry (input unit) 33, a display (display unit) 34, reference signal generation circuitry 35, transmission/reception circuitry 36, echo data processing circuitry 37, and image generation circuitry 38.

The processing circuitry 31 refers to, in addition to a special-purpose or general-purpose CPU (central processing unit) or MPU (micro processor unit), an application specific integrated circuit (ASIC), a programmable logic device, etc. Examples of the programmable logic device include a simple programmable logic device (SPLD), a complex programmable logic device (CPLD), and a field programmable gate array (FPGA). The processing circuitry 31 reads out and executes a program stored in the memory circuitry 32 or directly incorporated into the processing circuitry 31, thereby implementing functions 311 to 314 shown in FIG. 5.

Moreover, the processing circuitry 31 may be made up of a single circuit, or a combination of independent multiple circuits. In the latter case, a memory circuit that stores a program may be provided separately for each of the multiple circuits, or a single memory circuit may store programs corresponding to functions of the multiple circuits.

The memory circuitry 32 may be made up of a RAM (random access memory), a semiconductor memory element such as a flash memory, a hard disk, an optical disk, etc. The memory circuitry 32 may also be made up of a portable medium such as a USB (universal serial bus) memory, a DVD (digital video disk), etc. The memory circuitry 32 stores various processing programs (including applications programs as well as OS (operating system), etc.) to be used in the processing circuitry 31, data necessary for execution of programs, and medical images. Further, the OS may include GUI (graphical user interface) which heavily uses graphics for displaying information for the operator on the display 34, and enables fundamental operations by using the input circuitry 33.

The input circuitry 33 is a circuit that inputs signals from an input device such as a pointing device (mouse), a keyboard, etc., which can be operated by the operator, where it is supposed that the input device itself is included in the input circuitry 33. When the input device is operated by the operator, the input circuitry 33 generates an input signal corresponding to the operation and outputs it to the processing circuitry 31. Note that the apparatus main body 12 may include a touch panel in which the input device is integrally constructed with the display 34.

The display 34 includes a common display output apparatus such as a liquid crystal display and an OLED (organic light emitting diode) display, and displays image data generated by the image generation circuitry 38 according to control by the processing circuitry 31.

The reference signal generation circuitry 35 generates, for example, a continuous wave or a square wave, which has a frequency substantially equal to the center frequency of an ultrasonic pulse, to the transmission/reception circuitry 36 according to a control signal from the processing circuitry 31.

The transmission/reception circuitry 36 causes the ultrasonic probe 11 to perform transmission/reception according to a control signal from the processing circuitry 31. The transmission/reception circuitry 36 includes transmission circuitry 361 for creating a drive signal for causing transmission ultrasound to be radiated from the ultrasonic probe 11, and reception circuitry 362 for performing phasing addition on a received signal from the ultrasonic probe 11.

The transmission circuitry 361 includes a rate pulse generator, transmission delay circuitry, and a pulsar, which are not shown. The rate pulse generator creates a rate pulse for determining a repeating period of transmission ultrasound by frequency-dividing a continuous wave or square wave provided from the reference signal generation circuitry 35, and provides the rate pulse to the transmission delay circuitry. The transmission delay circuitry includes independent delay circuitries of the same number (N channels) as that of the transducers used for transmission, and gives the rate pulse a delay time for focusing transmission ultrasound at a predetermined depth to obtain a narrow beam width, and a delay time for radiating transmission ultrasound in a predetermined direction during transmission, and provides the rate pulse to the pulsar. The pulsar includes N channels of independent drive circuitries, and generates drive pulses for driving the transducers built in the ultrasonic probe 11, based on the rate pulse.

The reception circuitry 362 of the transmission/reception circuitry 36 includes a pre-amplifier, A/D (analog to digital) conversion circuitry, reception delay circuitry, and adding circuitry, which are not shown. The pre-amplifier includes N channels, and amplifies a minute signal which has been converted into a received electric signal by the transducer to ensure a sufficient S/N level. Each of the received signals of N channels, which has been amplified to a predetermined magnitude at the pre-amplifier, is converted into a digital signal at the A/D conversion circuitry, and is sent to the reception delay circuitry. The reception delay circuitry gives a focusing delay time for focusing ultrasound reflection wave from a predetermined depth, and a deflecting delay time for setting a reception directivity in a predetermined direction, to each of the received signals of N channels outputted from the A/D conversion circuitry. The adding circuitry performs phasing and adding of the received signals from the reception delay circuitry (matches the phases of received signals obtained from a predetermined direction and adds them together).

The echo data processing circuitry 37 performs processing to generate ultrasonic images on the echo data inputted from the reception circuitry 362, according to a control signal from the processing circuitry 31. For example, the echo data processing circuitry 37 performs B-mode processing such as logarithmic compression processing and envelope wave-detection processing, and Doppler processing such as orthogonal wave-detection processing and filtering processing.

The image generation circuitry 38 scans and converts data inputted from the echo data processing circuitry 37 with a scan converter according to a control signal from the processing circuitry 31, to generate ultrasonic image data. Then, the image generation circuitry 38 causes an ultrasonic image based on the ultrasonic image data to be displayed on the display 34. The ultrasonic image is, for example, a B-mode image and a color Doppler image.

Next, functions of the ultrasonic diagnostic apparatus 1 according to the first embodiment will be described.

Figure 5:
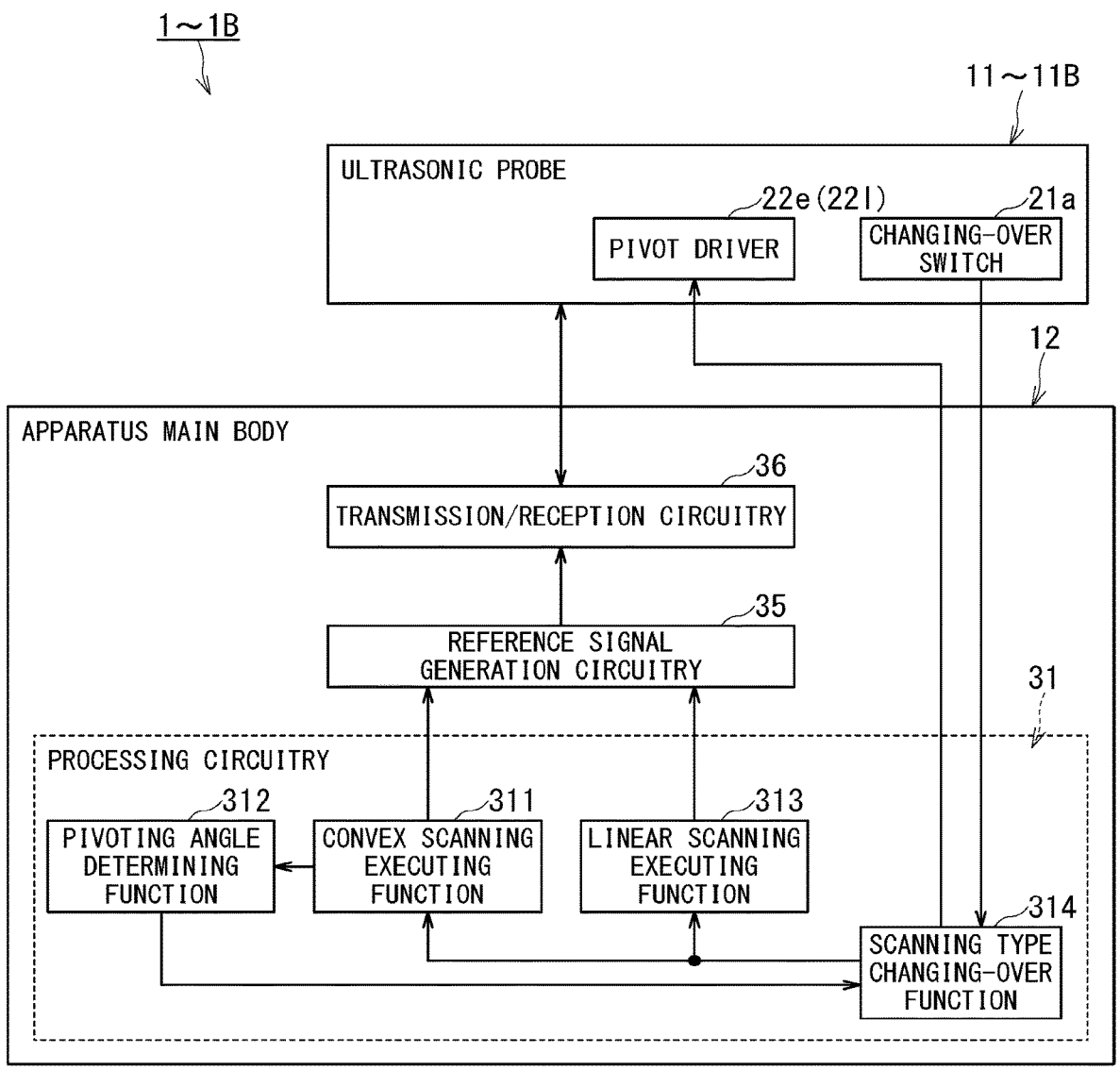
FIG. 5 is a block diagram showing functions of the ultrasonic diagnostic apparatus according to the first embodiment.

FIG. 5 is a block diagram showing functions of the ultrasonic diagnostic apparatus 1 according to the first embodiment.

As a result of the processing circuitry 31 performing a program, the ultrasonic diagnostic apparatus 1 functions as a convex scanning executing function 311, a pivoting angle determining function 312, a linear scanning executing function 313, and a scanning type changing-over function 314. Note that although description will be made taking as an example a case in which the functions 311 to 314 function in a software fashion, the whole or part of those functions 311 to 314 may be installed in a hardware fashion, respectively in the ultrasonic diagnostic apparatus 1.

Figure 8:
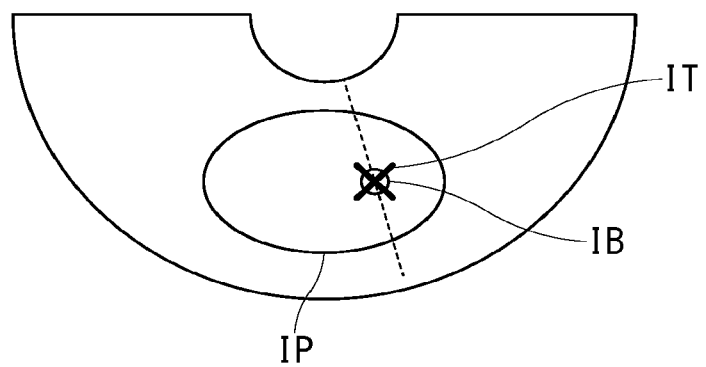
FIG. 8 is a diagram showing an example of an ultrasonic image by the convex scanning.

The convex scanning executing function 311 is a function of controlling the convex array 22b of the ultrasonic probe 11, thereby causing a convex scanning to be executed. The convex scanning is executed such that the operator can confirm the insertion position of the puncture needle into an organ, for example, the prostate, on an ultrasonic image. An ultrasonic image by the convex scanning is shown in FIG. 8.

The pivoting angle determining function 312 is a function of determining a pivoting angle in a change-over of the scanning type by the scanning type changing-over function 314 based on the position of a puncture target to be set on an ultrasonic image by the convex scanning executing function 311.

Figure 10:
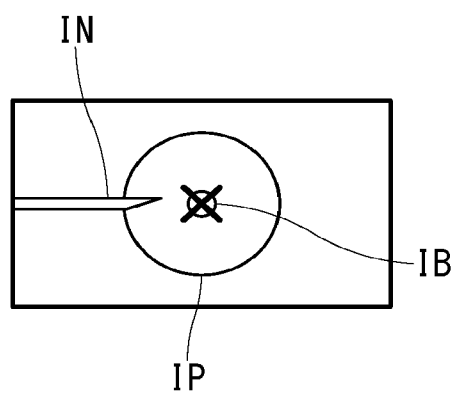
FIG. 10 is a diagram showing an example of an ultrasonic image by the linear scanning.

The linear scanning executing function 313 is a function of controlling the linear array 22a of the ultrasonic probe 11, thereby causing a linear scanning to be performed. The linear scanning is performed such that the operator can confirm a puncture target and a puncture needle on an ultrasonic image viewed from a side of the puncture needle. An ultrasonic image by liner scanning is shown in FIG. 10.

The scanning type changing-over function 314 includes a function of controlling a pivot driver 22e such that upon depression of the changing-over switch 21a of the ultrasonic probe 11 during execution of the convex scanning by the convex scanning executing function 311, the pivot shaft 22d pivots (pivots in positive direction) according to a pivoting angle determined by the pivoting angle determining function 312, and a function of changing over the scanning type from the convex scanning to the linear scanning. Moreover, the scanning type changing-over function 314 includes a function of controlling the pivot driver 22e such that upon depression of the changing-over switch 21a of the ultrasonic probe 11 during execution of the linear scanning by the linear scanning executing function 313, the pivot shaft 22d pivots (pivots in a negative direction) according to a pivoting angle determined by the pivoting angle determining function 312, and a function of changing over the scanning type from the linear scanning to the convex scanning.

For example, consider a case in which the pivot shaft 22d (arrays 22a and 22b) repeats puncturing to three puncture targets. In such a case, in puncturing to a first puncture target, the scanning type changing-over function 314 rotates the pivot shaft 22d by a first pivoting angle θ1 in a positive direction, and thereafter rotates the pivot shaft 22d by the same first pivoting angle θ1 in a negative direction. In the following puncturing to a second puncture target, the scanning type changing-over function 314 rotates the pivot shaft 22d by a second pivoting angle θ2 in a positive direction, and thereafter rotates the pivot shaft 22d by the same pivoting angle θ2 in a negative direction. In the following puncturing to a third puncture target, the scanning type changing-over function 314 rotates the pivot shaft 22d by a third pivoting angle θ3 in a positive direction, and thereafter rotates the pivot shaft 22d by the same third pivoting angle θ3 in a negative direction.

Where, the pivoting angle determining function 312 is not an essential function for the ultrasonic diagnostic apparatus 1. When the pivoting angle determining function 312 is absent, and when the changing-over switch 21a of the ultrasonic probe 11 is depressed during execution of the convex scanning by the convex scanning executing function 311, the pivot shaft 22d pivots (pivots in a positive direction) according to a previously set, fixed pivoting angle. Moreover, when the pivoting angle determining function 312 is absent, and when the changing-over switch 21a of the ultrasonic probe 11 is depressed during execution of the linear scanning by the linear scanning executing function 313, the pivot shaft 22d pivots (pivots in the negative direction) according to a previously set, fixed pivoting angle.

For example, consider a case in which the pivoting angle determining function 312 is absent, and the pivot shaft 22d (arrays 22a and 22b) repeats puncturing to three puncture targets. In such a case, the pivoting angle θ of the pivot shaft 22d is supposed to be a previously set angle α (shown in FIG. 7), and in the puncturing to the first puncture target, the pivot shaft 22d pivots by a pivoting angle α in the positive direction, and thereafter pivots by the same pivoting angle α in the negative direction. In the following puncturing to the second puncture target, the pivot shaft 22d pivots by the same pivoting angle α in the positive direction, and thereafter pivots by the same pivoting angle α in the negative direction. In the following puncturing to the third puncture target, the pivot shaft 22d pivots by the same pivoting angle α in the positive direction, and thereafter pivots by the same pivoting angle α in the negative direction.

Next, an operation of the ultrasonic diagnostic apparatus 1 according to the first embodiment will be described by using FIGS. 1 and 6.

Figure 6:
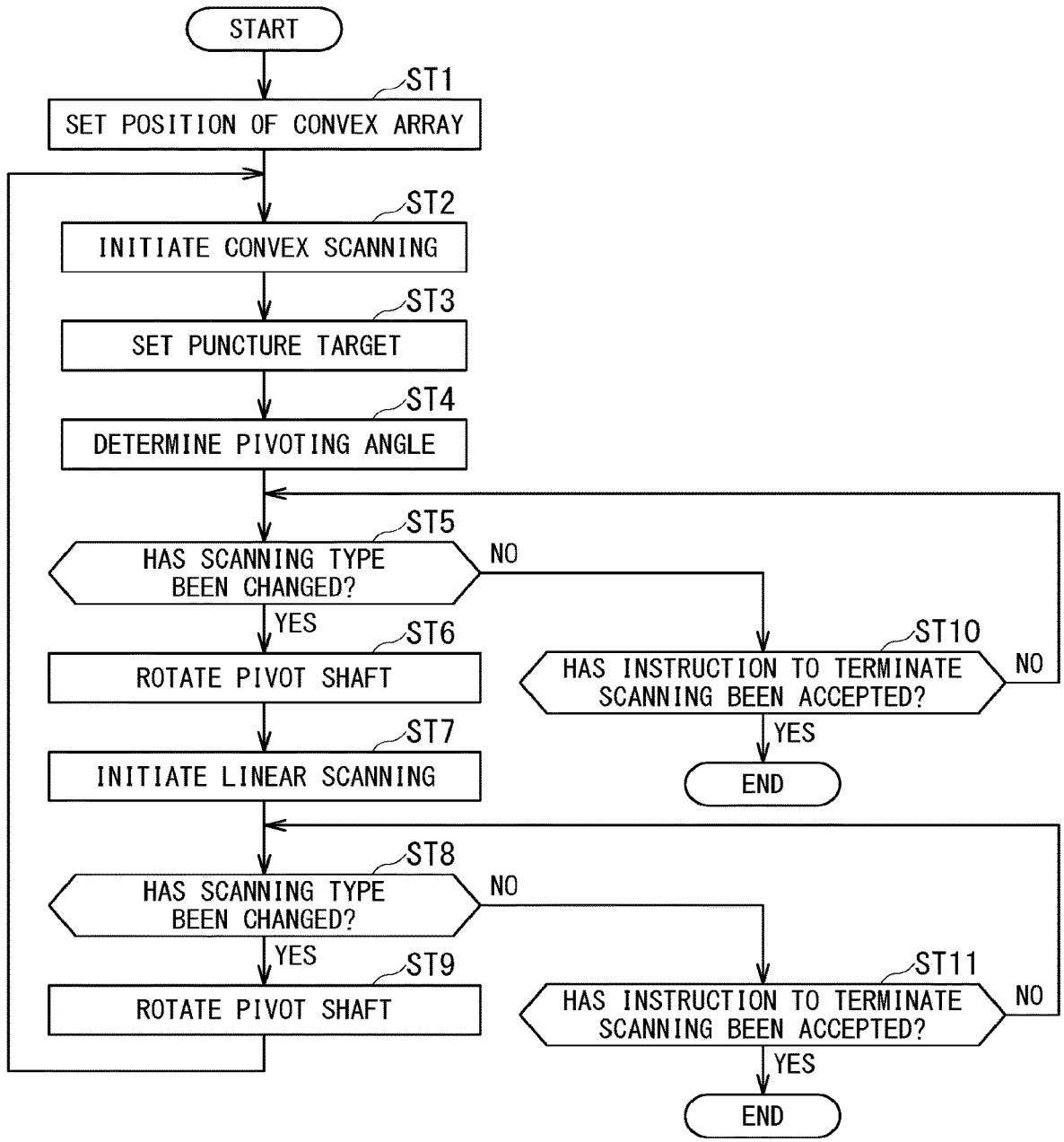
FIG. 6 is a flowchart showing the operation of the ultrasonic diagnostic apparatus according to the first embodiment.

FIG. 6 is a flowchart showing the operation of the ultrasonic diagnostic apparatus 1 according to the first embodiment.

The ultrasonic diagnostic apparatus 1 sets, when an instruction to initiate scanning via the input circuitry 33 is input, the position of the convex array 22b such that the scanning type of the ultrasonic probe 11 is the convex scanning (step ST1).

The ultrasonic diagnostic apparatus 1 controls the convex array 22b of the ultrasonic probe 11 such that the operator can confirm the insertion position of the puncture needle into an organ, for example, the prostate, on an ultrasonic image, and initiates the convex scanning (step ST2). The ultrasonic diagnostic apparatus 1 sets a puncture target on an ultrasonic image by the convex scanning initiated by step ST2 (step ST3).

Figure 7:
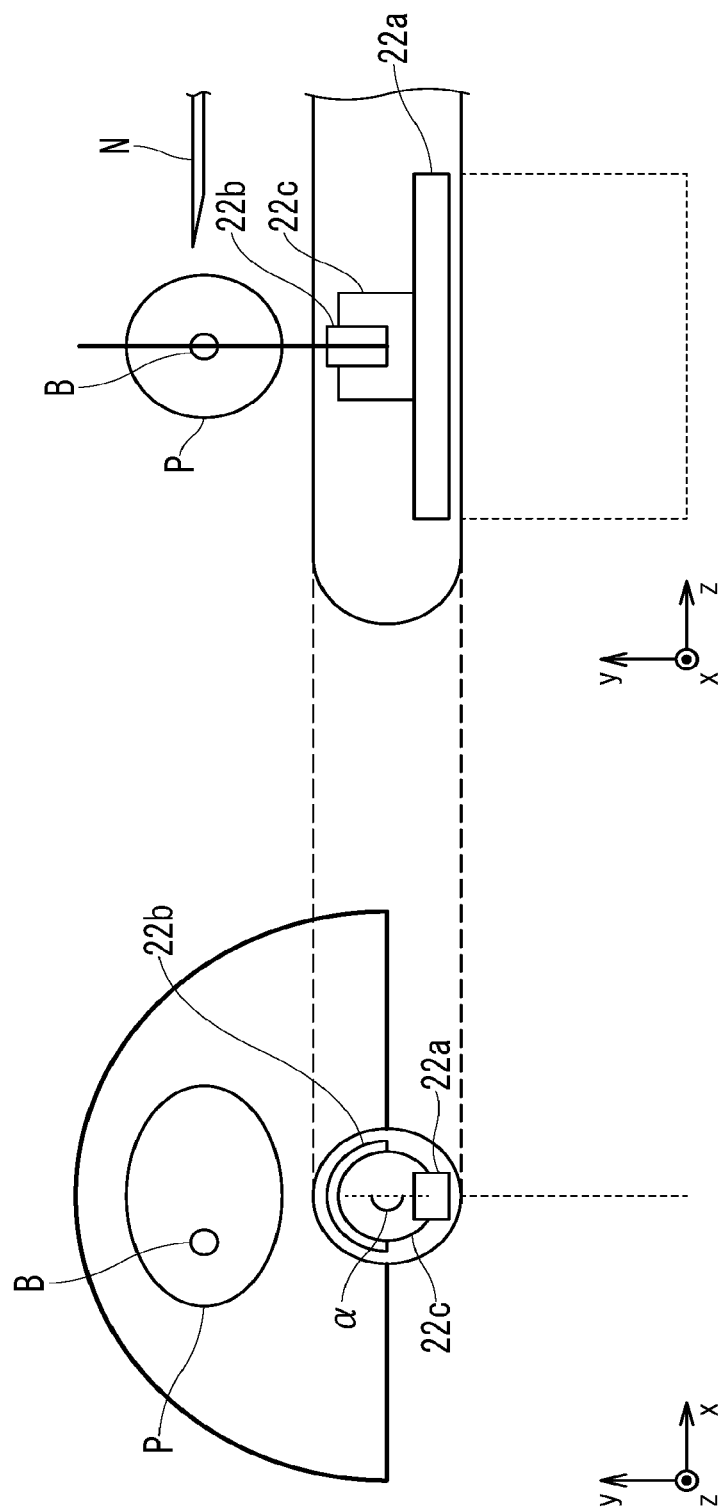
FIG. 7 is a diagram to illustrate a convex scanning.

FIG. 7 is a diagram to illustrate the convex scanning. FIG. 8 is a diagram showing an example of an ultrasonic image by the convex scanning.

FIG. 7 shows a prostate P as an organ, and a region of interest B which is a region where presence of a prostate cancer included in the prostate P is suspected. When the convex scanning is performed on the prostate P, an ultrasonic image of an x-y section shown in FIG. 8 is obtained. The ultrasonic image shown in FIG. 8 includes a prostate image IP which corresponds to the prostate P shown in FIG. 7, a region-of-interest image IB which corresponds to the region of interest B, and a puncture target IT as a target.

Where, the puncture target IT may be set on the region-of-interest image IB by the operator, or the position of a candidate, which is selected from predetermined candidates of puncture target which are superimposed on the ultrasonic image, may be set as the position of the puncture target. In such a case, candidates of puncture target are superimposed on an ultrasonic image generated through the convex scanning, at positions corresponding to the positions of through holes for guiding a puncture needle in the puncture adaptor 24 (shown in FIGS. 2 to 4).

The operator can advance the puncture needle N while viewing a substantially real-time ultrasonic image shown in FIG. 8.

Moreover, a marker of a scanning plane by the linear scanning may be superimposed on an ultrasonic image by the convex scanning. The marker is shown by a dotted line in FIG. 8.

Referring back to description of FIGS. 1 and 6, the ultrasonic diagnostic apparatus 1 determines a pivoting angle in the change-over of scanning type, based on the position of the puncture target set on the ultrasonic image by the convex scanning (step ST4). The ultrasonic diagnostic apparatus 1 judges whether or not the scanning type has been changed over from convex scanning to linear scanning via the changing-over switch 21a (shown in FIGS. 2 to 4) (step ST5).

When it is judged to be YES in step ST5, that is, that the scanning type has been changed over from the convex scanning to the linear scanning, the ultrasonic diagnostic apparatus 1 terminates the convex scanning, and rotates the pivot shaft 22d (rotates the pivot shaft 22d in the positive direction) according to a pivoting angle determined by step ST4 (step ST6). The pivoting angle in step ST6 is determined such that the scanning center by the linear scanning corresponds to the position of the puncture target set by step ST3.

The ultrasonic diagnostic apparatus 1 controls the linear array 22a of the ultrasonic probe 11 such that the operator can confirm the puncture target and the puncture needle on an ultrasonic image viewed from a side of the puncture needle, and initiates the linear scanning (step ST7).

Figure 9:
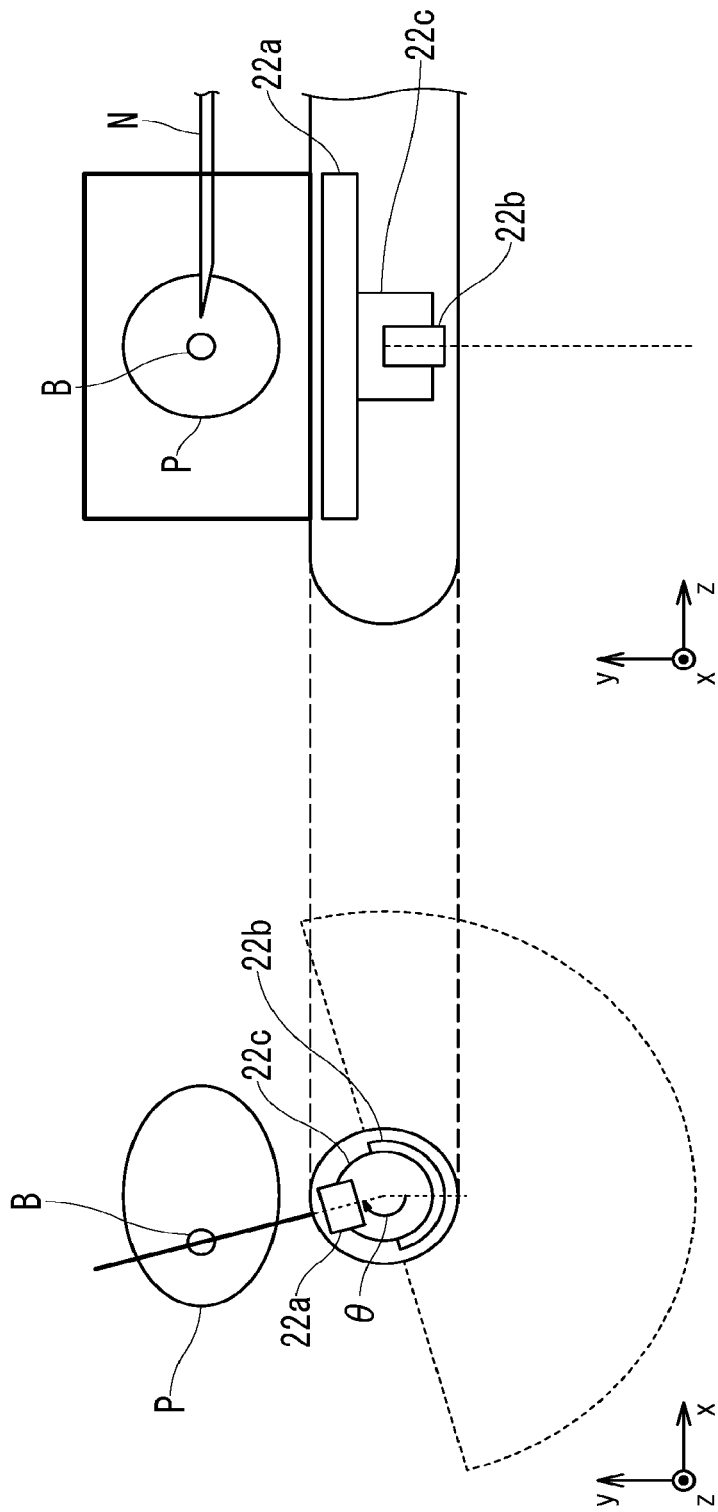
FIG. 9 is a diagram to illustrate a linear scanning.

FIG. 9 is a diagram to illustrate the linear scanning. FIG. 10 is a diagram showing an example of an ultrasonic image by the linear scanning.

FIG. 9 shows a state in which the arrays 22a and 22b shown in FIG. 7 are rotated by a pivoting angle θ around the axis of the pivot shaft 22d. FIG. 9 shows a prostate P as an organ and a region of interest B included in the prostate P. When the linear scanning on the prostate P is performed, an ultrasonic image of a y-z section shown in FIG. 10 will be obtained. The ultrasonic image shown in FIG. 10 includes a prostate image IP corresponding to the prostate P shown in FIG. 9, a region-of-interest image IB corresponding to the region of interest B, a puncture target IT, and a puncture needle IN.

The operator can advance the puncture needle N while viewing a substantially real-time ultrasonic image shown in FIG. 10.

Referring back to description of FIGS. 1 and 6, the ultrasonic diagnostic apparatus 1 judges whether or not the scanning type has been changed over from the linear scanning to the convex scanning through the changing-over switch 21a (shown in FIGS. 2 to 4) (step ST8).

When it is judged to be YES at step ST8, that is, that the scanning type has been changed over from the linear scanning to the convex scanning, the ultrasonic diagnostic apparatus 1 terminates the linear scanning, and rotates the pivot shaft 22d (rotates the pivot shaft 22d in the negative direction) according to a pivoting angle determined by step ST4 (or a previously set, fixed pivoting angle) (step ST9). The ultrasonic diagnostic apparatus 1 controls the convex array 22b of the ultrasonic probe 11 to initiate the convex scanning (step ST2).

The ultrasonic diagnostic apparatus 1 controls the linear array 22a of the ultrasonic probe 11 to initiate the linear scanning (step ST7), and controls the convex array 22b of the ultrasonic probe 11 to initiate the convex scanning (step ST2).

On the other hand, when it is judged to be NO at step ST5, that is, that the scanning type has not been changed over from the convex scanning to the linear scanning, the ultrasonic diagnostic apparatus 1 judges whether or not an instruction to terminate scanning has been accepted (step ST10). When it is judged to be YES at step ST10, that is, that an instruction to terminate scanning has been accepted, the ultrasonic diagnostic apparatus 1 terminates scanning. On the other hand, when it is judged to be NO at step ST10, that is, that no instruction to terminate scanning has been accepted, the ultrasonic diagnostic apparatus 1 returns to judgment at step ST5.

Moreover, when it is judged to be NO at step ST8, that is, that the scanning type has not been changed over from the linear scanning to the convex scanning, the ultrasonic diagnostic apparatus 1 judges whether or not an instruction to terminate scanning has been accepted (step ST11). When it is judged to be YES at step ST11, that is, that an instruction to terminate scanning has been accepted, the ultrasonic diagnostic apparatus 1 terminates scanning. On the other hand, when it is judged to be NO at step ST11, that is, that no instruction to terminate scanning has been accepted, the ultrasonic diagnostic apparatus 1 returns to judgment of step ST8.

For example, consider a case in which the ultrasonic diagnostic apparatus 1 repeats operations of steps ST2 to ST9 shown in FIG. 6 for three puncture targets (three pivoting angles θ1 to θ3). In that case, the ultrasonic diagnostic apparatus 1 rotates the pivot shaft 22d (arrays 22a and 22b) by a first pivoting angle θ1 in the positive direction at step ST6 of a first period, and thereafter rotates the pivot shaft 22d by the first pivoting angle θ1 in the negative direction at step ST9. The ultrasonic diagnostic apparatus 1 rotates the pivot shaft 22d by a second pivoting angle θ2 in the positive direction at step ST6 in the following second period, and thereafter rotates the pivot shaft 22d by the second pivoting angle θ2 in the negative direction at step ST9. The ultrasonic diagnostic apparatus 1 rotates the pivot shaft 22d by a third pivoting angle θ3 in the positive direction at step ST6 in the following third period, and thereafter rotates the pivot shaft 22d by the third pivoting angle θ3 in the negative direction at step ST9.

Note that although description has been made using FIGS. 7 to 10 on a case in which the region of interest B is a prostate cancer (malignant tumor), and a target to be set on a region-of-interest image IB relating to the region of interest B is the puncture target, the present embodiment will not be limited in such a case. For example, the region of interest B may be a tumor of prostate, and a target to be set on a region-of-interest image IB may be a measurement target. In that case, an orthogonal section image, that is, an ultrasonic image by the convex scanning initiated by step ST2, and an ultrasonic image by the linear scanning initiated by step ST7 may be displayed, and the size and dimensions etc. of the region-of-interest image IB are measured based on an orthogonal sectional image.

Moreover, the region of interest B is not limited to a tumor of prostate. For example, the region of interest B may be a tumor of ovarian.

According to the ultrasonic diagnostic apparatus 1 relating to the first embodiment, since change over between the first transducer set 22a and the second transducer set 22b is automatically performed, it is possible to improve operability by the operator.

Further, according to the ultrasonic diagnostic apparatus 1 relating to the first embodiment, it is possible to cause the puncture target, which has appeared on a scanning plane by either of the transducer sets, to appear on a scanning plane by another of the transducer sets after change over.

Second Embodiment

Since the configurations of the ultrasonic probe and the ultrasonic diagnostic apparatus according to the second embodiment are equal to those of the ultrasonic probe and the ultrasonic diagnostic apparatus according to the first embodiment shown in FIG. 1, illustration and description thereof will be omitted.

Figure 11:
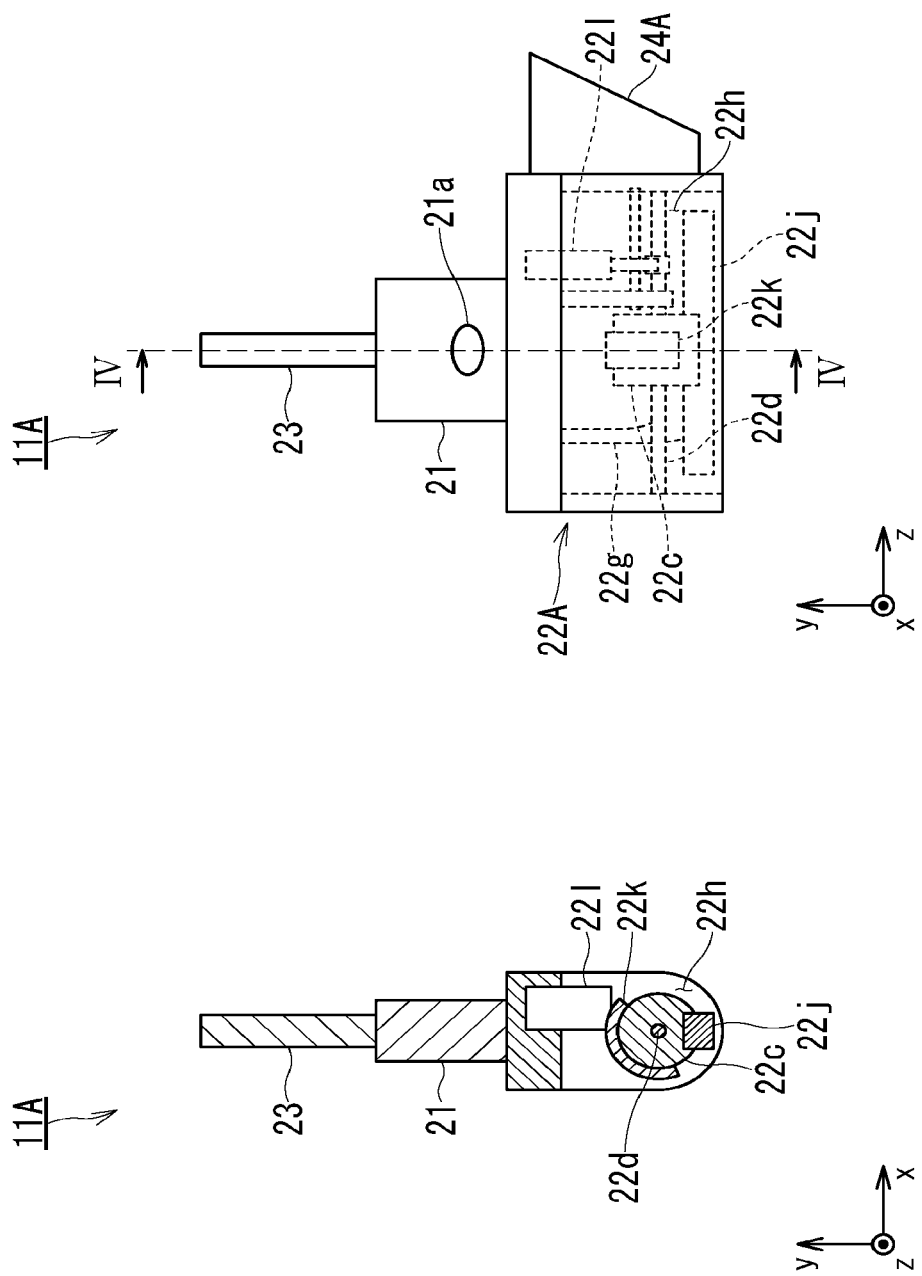
FIG. 11 is a diagram showing an example structure of an ultrasonic probe according to a second embodiment.

FIG. 11 is a diagram showing an example structure of an ultrasonic probe according to a second embodiment.

FIG. 11 shows an ultrasonic probe 11A according to the second embodiment. The ultrasonic probe 11A is a probe for use on body surfaces. The ultrasonic probe 11A performs transmission/reception of ultrasound to and from an object according to control by the apparatus main body 12.

Shown on the left-hand side of FIG. 11 is a IV-IV section (x-y section) of the ultrasonic probe 11A shown on the right-hand side of FIG. 11, and shown on the right-hand side of FIG. 11 is a side view (viewed from a y-z plane) of the ultrasonic probe 11A.

The ultrasonic probe 11A includes a handle portion 21, a probe body (distal end portion) 22A, and a cable 23.

Further, the ultrasonic probe 11A may be equipped with a puncture adaptor 24A for guiding a puncture needle. A through hole for guiding the puncture needle is formed at a predetermined position of the puncture adaptor 24A.

The probe body 22A includes a transducer set supporter 22c, a pivot shaft 22d, an acoustic window (not shown), a signal line 22g, a solution layer 22h, a first transducer set 22j, a second transducer set 22k, and a pivot driver (electromagnet) 221. It is supposed that scanning types by the first transducer set 22j and by the second transducer set 22k are different from each other.

Note that in the ultrasonic probe 11A shown in FIG. 11, the same components as those of the ultrasonic probe 11 shown in FIG. 2 are given the same reference symbols, thereby omitting description thereof.

A center position, in a direction (z direction) orthogonal to an axis of the probe body 22A, of the second transducer set 22k of the ultrasonic probe 11A substantially corresponds to a center position in the z direction, of the first transducer set 22j. Moreover, in an orthogonal plane (x-y section) with respect to the z direction, an angle (β shown in FIG. 12) formed between a scanning plane of the first transducer set 22j and a center line of the second transducer set 22k is preferably not more than 180°. This is because the puncture needle advances obliquely to, not in parallel with, the z direction when the ultrasonic probe 11A is used.

The first transducer set 22j has a structure in which transducers are arranged in a row along the z direction. The row along the z direction may be one or more rows. Each transducer is an electro-acoustic transducer, which has a function of converting an electric pulse into an ultrasonic pulse (transmission ultrasound) during transmission, and converting an ultrasonic reflected wave into an electric signal during reception. The first transducer set 22j is, for example, a linear array. Hereafter, description will be made taking as an example a case in which the first transducer set 22j is a linear array.

When transducers are arranged in 1 to about 3 rows in the linear array 22j, a lens member (not shown) for focusing ultrasound in the x direction is provided in a front side of the linear array 22j. On the other hand, when transducers are arranged in a sufficient number of rows in the linear array 22j, electronic focusing is used to focus ultrasound in the x direction.

The second transducer set 22k has a structure in which transducers are arranged on a plane (x-y section) substantially orthogonal to the z direction. The second transducer set 22k includes the transducers arranged on the one plane substantially orthogonal to the z direction or on multiple planes substantially orthogonal to the z direction. The second transducer set 22k is, for example, a convex array in which transducers are arranged on a plane substantially orthogonal to the z direction, and in a portion of a circumference whose radius of curvature substantially corresponds to the pivoting radius. Hereafter, description will be made taking as an example a case in which the second transducer set 22k is a convex array.

When the transducers are arranged in 1 to about 3 planes in the convex array 22k, a lens member (not shown) for focusing ultrasound in the z direction is provided in a front side of the convex array 22k. On the other hand, when the transducers are arranged in a sufficient number of planes in the convex array 22k, electronic focusing is used to focus ultrasound in the z direction.

Note that although it is supposed that a bucking for preventing back reflection is provided in a rear side of each of the arrays 22j and 22k, description thereof will be omitted.

The pivot driver 221 rotates the pivot shaft 22d according to a pivoting angle instructed from the apparatus main body 12 upon depression of the changing-over switch 21a. Note that, upon depression of the changing-over switch 21a, the pivot driver 221 may rotates the pivot shaft 22d according to a previously set, fixed pivoting angle.

Since the functions of the ultrasonic diagnostic apparatus 1A according to the second embodiment are equal to those of the ultrasonic diagnostic apparatus 1 according to the first embodiment shown in FIG. 5, description thereof will be omitted. Moreover, since the operations of the ultrasonic diagnostic apparatus 1A according to the second embodiment are equal to those of the ultrasonic diagnostic apparatus 1 according to the first embodiment shown in FIG. 6, description thereof will be omitted.

Figure 12:
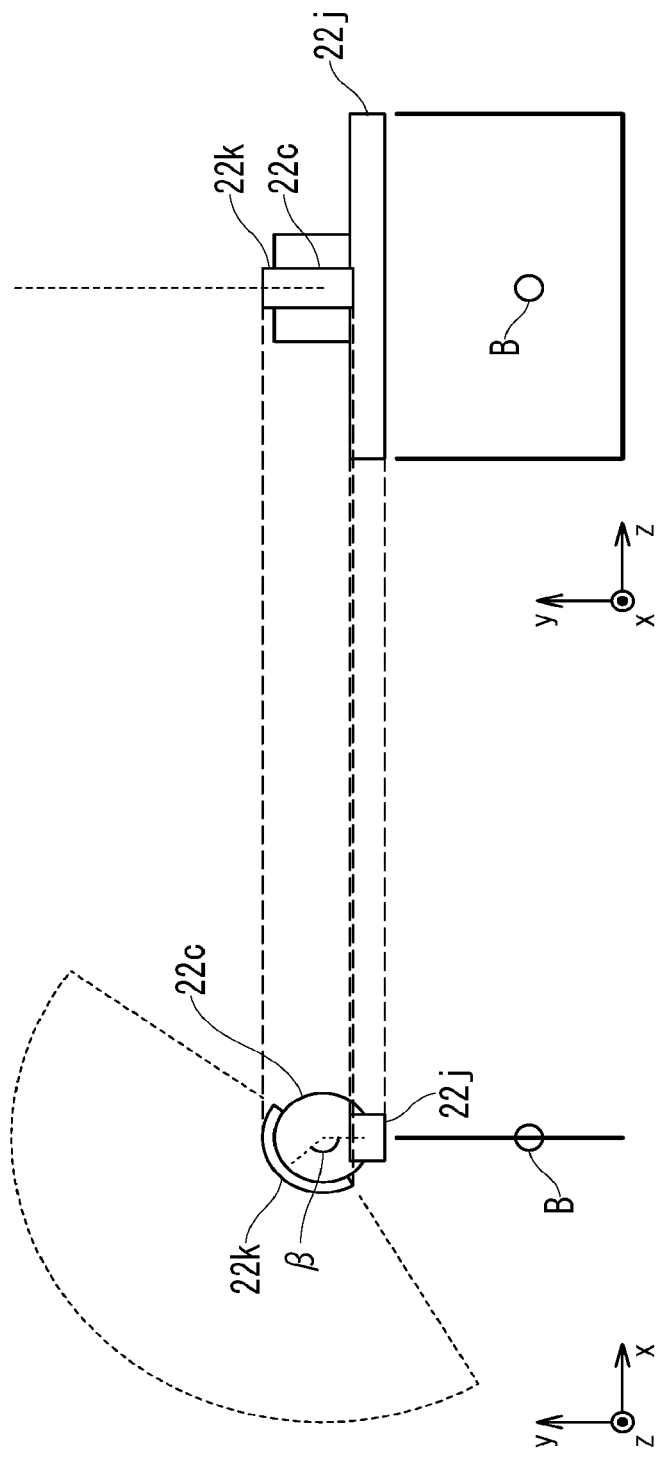
FIG. 12 is a diagram to illustrate a linear scanning.
Figure 13:
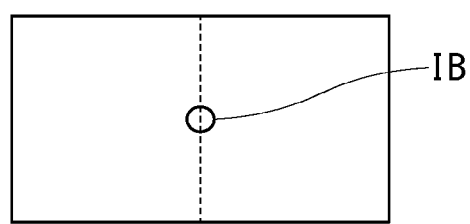
FIG. 13 is a diagram showing an example of an ultrasonic image by the linear scanning.

FIG. 12 is a diagram to illustrate the linear scanning. FIG. 13 is a diagram showing an example of an ultrasonic image by the linear scanning.

FIG. 12 shows a region of interest B. Performing the linear scanning from a body surface will result in an ultrasonic image of a y-z section shown in FIG. 13. The ultrasonic image shown in FIG. 13 includes a region-of-interest image IB corresponding to the region of interest B shown in FIG. 12. The operator can advance the puncture needle N while viewing a substantially real-time ultrasonic image shown in FIG. 13.

Moreover, a marker of a scanning plane by the convex scanning may be superimposed on an ultrasonic image by the linear scanning. The marker is shown by a dotted line in FIG. 13.

Figure 14:
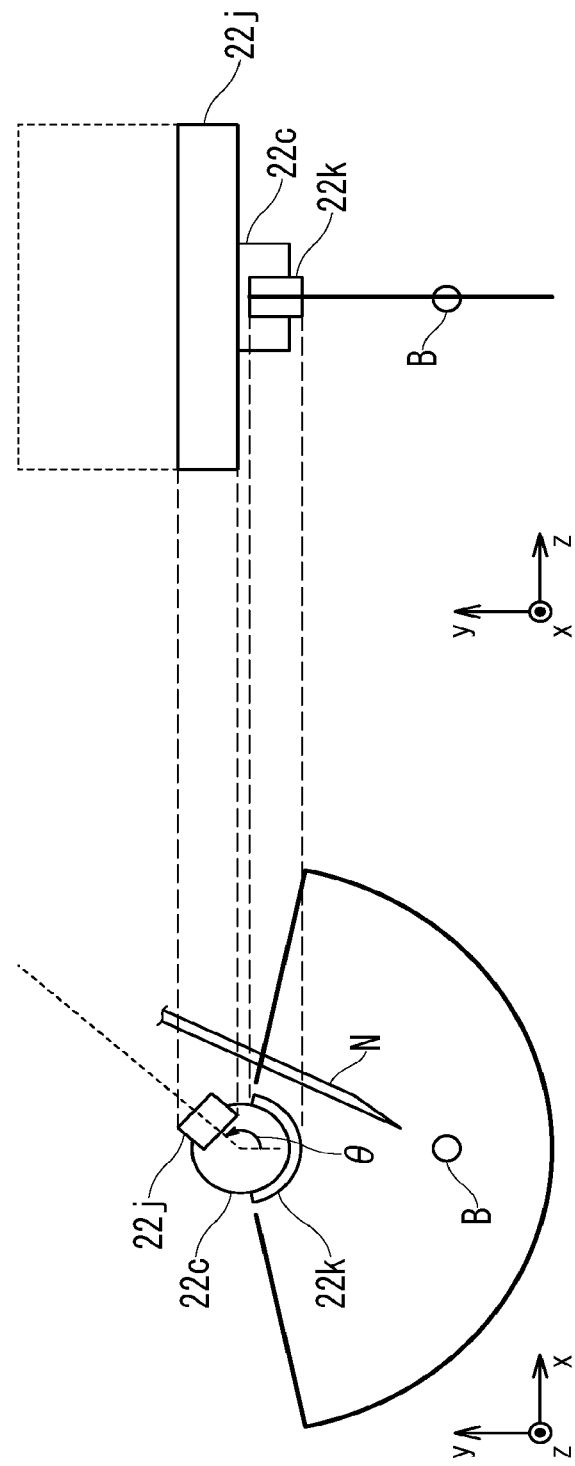
FIG. 14 is a diagram to illustrate a convex scanning.
Figure 15:
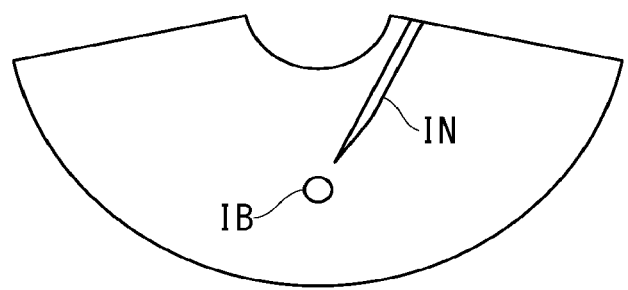
FIG. 15 is a diagram showing an example of an ultrasonic image by the convex scanning.

FIG. 14 is a diagram to illustrate the convex scanning. FIG. 15 is a diagram showing an example of an ultrasonic image by the convex scanning.

FIG. 14 shows a state in which the arrays 22*j* and 22*k* shown in FIG. 12 pivot by a pivoting angle θ around the axis of the pivot shaft 22*d*. FIG. 14 shows a region of interest B. Performing the linear scanning from a body surface will result in an ultrasonic image of an x-y section shown in FIG. 15. The ultrasonic image shown in FIG. 15 includes a region-of-interest image IB corresponding to the region of interest B shown in FIG. 14, and a puncture needle IN. The operator can advance the puncture needle N while viewing a substantially real-time ultrasonic image shown in FIG. 15.

According to the ultrasonic diagnostic apparatus 1A relating to the second embodiment, since change-over between the first transducer set 22*j* and the second transducer set 22*k* is automatically performed, it is possible to improve operability by the operator.

Further, according to the ultrasonic diagnostic apparatus 1A relating to the second embodiment, it is possible to cause a puncture target, which has appeared on a scanning plane by either of the transducer sets, to appear on a scanning plane by another of the transducer sets after change over.

Third Embodiment

Since the configurations of the ultrasonic probe and the ultrasonic diagnostic apparatus according to a third embodiment are equal to those of the ultrasonic probe and the ultrasonic diagnostic apparatus according to the first embodiment shown in FIG. 1, illustration and description thereof will be omitted.

Figure 16:
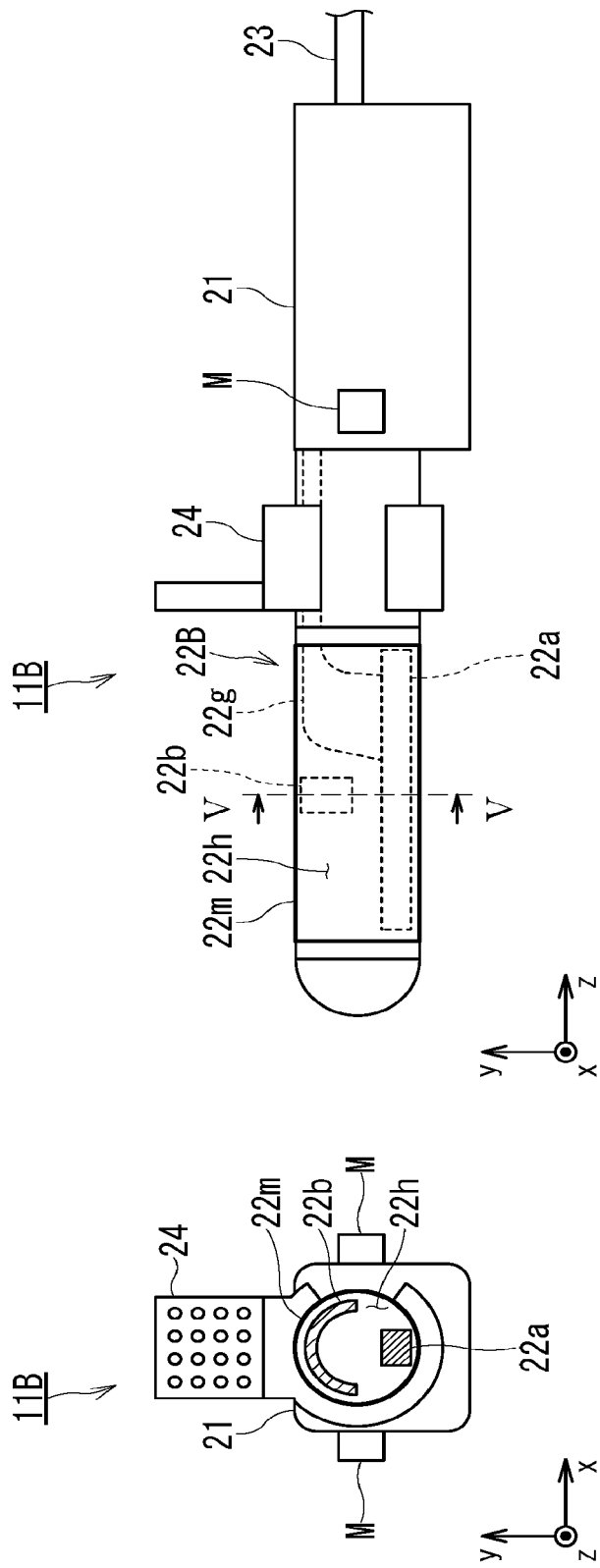
FIG. 16 is a diagram showing an example structure of an ultrasonic probe according to a third embodiment.

FIG. 16 is a diagram to show an example structure of an ultrasonic probe according to the third embodiment.

FIG. 16 shows an ultrasonic probe 11B according to the third embodiment. The ultrasonic probe 11B is one principally for use inside a body cavity, which is suitable for being inserted through the rectum to image an internal organ. The ultrasonic probe 11B performs transmission/reception of ultrasound to and from an object according to control by the apparatus main body 12.

Shown on the left-hand side of FIG. 16 is a V-V section (x-y section) of the ultrasonic probe 11B shown on the right-hand side of FIG. 16, and shown on the right-hand side of FIG. 16 is a side view (viewed from a y-z plane) of the ultrasonic probe 11B.

The ultrasonic probe 11B includes a handle portion 21, a probe body (distal end portion) 22B, and a cable 23.

Further, the ultrasonic probe 11B may be equipped with a puncture adaptor 24 for guiding a puncture needle. Through holes for guiding a puncture needle are formed at predetermined positions of the puncture adaptor 24. The ultrasonic probe 11B can be equipped with two position sensors (magnetic sensors) M that measure a position of the ultrasonic probe 11B, a direction of the axis of the ultrasonic probe 11B, and a pivoting angle of the ultrasonic probe 11B.

The probe body 22B includes a first transducer set 22*a*, a second transducer set 22*b*, a signal line 22*g*, a solution layer 22*h*, and an acoustic window 22*m*. It is supposed that scanning types by the first transducer set 22*a* and by the second transducer set 22*b* are different from each other.

Note that in the ultrasonic probe 11B shown in FIG. 16, the same components as those of the ultrasonic probe 11 shown in FIG. 2 are given the same reference symbols, thereby omitting description thereof.

The acoustic window 22*m* is provided in the whole or a part (a portion of transmission/reception opening) of a circumference around the axis of the probe body 22B out of the housing, which is in direct contact with the object, and is made of a material which easily transmits ultrasound. The housing accommodates a linear array 22*a*, a convex array 22*b*, and part of signal line 22*g*.

The ultrasonic diagnostic apparatus 1B is configured such that when a manual rotating operation for changing-over the scanning type is performed by the operator, a scanning plane by the scanning type after the change-over is guided so as to include the position of the puncture target IT (shown in FIG. 8) which has been set on an ultrasonic image by the scanning type before the change-over. When the scanning plane by the scanning type after the change-over includes the position of the puncture target IT, the ultrasonic diagnostic apparatus 1B performs notification (by at least one of display and voice) of that fact.

A transmitter (magnetic transmitter) is disposed proximal to the ultrasonic diagnostic apparatus 1B. Magnetic fields in three dimensional directions are temporally changed over and radiated from the transmitter and, in synchronous with that, the position sensor M detects the three-dimensional coordinates, making it possible that the ultrasonic diagnostic apparatus 1B measures the pivoting angle of the ultrasonic probe 11B.

Since the ultrasonic diagnostic apparatus 1B can calculate the spatial position of the puncture target IT (shown in FIG. 8) set on an ultrasonic image by the convex scanning, it can calculate a target pivoting angle when the scanning plane by the linear scanning includes the puncture target IT. Then, the ultrasonic diagnostic apparatus 1B can perform notification of when a measured pivoting angle of the ultrasonic probe 11B resulted from the manual rotating operation substantially corresponds to the target pivoting angle.

Note that as a result of the position sensor M detecting three dimensional coordinates, the ultrasonic diagnostic apparatus 1B can also measure the spatial position of the ultrasonic probe 11B and the direction of the axis of the ultrasonic probe 11B. In that case, although, if the position of the ultrasonic probe 11B and the direction of the axis of the ultrasonic probe 11B change during the manual rotating operation of the ultrasonic probe 11B, measured position of the ultrasonic probe 11B, and measured direction of the axis of the ultrasonic probe 11B will change, it is possible to comprehensively estimate such changes and perform notification when the scanning plane by the linear scanning includes a puncture target IT (shown in FIG. 8).

According to the ultrasonic diagnostic apparatus 1B relating to the third embodiment, it is possible to cause the puncture target, which has appeared on a scanning plane by either of the transducer sets, to appear on a scanning plane by another of the transducer sets after change over.

According to the ultrasonic probe and ultrasonic diagnostic apparatus relating to at least one of the above described embodiments, it is possible to improve operability by the operator.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An ultrasonic probe, comprising:
   a first transducer set in which first transducers are arranged in a direction parallel to an axis of the ultrasonic probe;
   a second transducer set in which second transducers are arranged on a plane orthogonal to the axis; and
   a pivot shaft supporting the first transducer set and the second transducer set, and configured to pivot around the axis, wherein
   the second transducer set is configured to be slidable on and along the pivot shaft,
   the first transducers of the first transducer set are arranged in a linear array and perform a linear scanning, and
   the second transducers of the second transducer set are arranged in a convex array and perform a convex scanning.

2. The ultrasonic probe according to claim 1, wherein a center position of the first transducer set in the direction parallel to the axis and a center position of the second transducer set in the direction parallel to the axis are different from each other.

3. The ultrasonic probe according to claim 1, wherein the first transducer set and the second transducer set perform different types of scanning from each other, and a center position of the first transducer set in the direction parallel to the axis and a center position of the second transducer set in the direction parallel to the axis are different from each other.

4. The ultrasonic probe according to claim 1, wherein the first transducer set and the second transducer set are covered by a housing, and an interior of the housing is filled with liquid or fluid matter.

5. The ultrasonic probe according to claim 4, wherein a pivoting center of the pivot shaft corresponds to an axis of the housing.

6. The ultrasonic probe according to claim 1, wherein the pivot shaft pivots using an electric motor or an electromagnet.

7. The ultrasonic probe according to claim 1, further comprising
   a scale indicating a pivoting angle of the pivot shaft.

8. The ultrasonic probe according to claim 1, further comprising
   a changing-over switch for instructing the pivot shaft to pivot.

9. The ultrasonic probe according to claim 1, wherein the second transducer set includes the second transducers arranged on a circumference around the axis and arranged on a plane orthogonal to the axis, and the second transducer set is insertable into a body cavity to collect an ultrasonic image of an inside of the body cavity.

10. An ultrasonic diagnostic apparatus, comprising:
    the ultrasonic probe according to claim 1; and
    processing circuitry configured to:
    perform a first scanning by the first transducer set to generate a first ultrasonic image and a second scanning by the second transducer set to generate a second ultrasonic image through the ultrasonic probe;
    display at least the second ultrasonic image on a display;
    set, when a region of the displayed second ultrasonic image generated through the second scanning is specified as a target, a pivoting angle such that a scanning center which is a center of the region which is to be scanned by the first transducer set corresponds to a position of the target based on the position of the target; and
    control a pivoting of the pivot shaft according to the pivoting angle.

11. The ultrasonic diagnostic apparatus according to claim 10, wherein
    the processing circuitry is configured to superimpose a linear marker indicating a scanning plane of the first scanning on the second ultrasonic image generated through the second scanning.

12. The ultrasonic diagnostic apparatus according to claim 10, wherein the processing circuitry is configured to:
    superimpose on the second ultrasonic image generated through the second scanning candidate targets to be set as the target; and
    set a position of a candidate target selected from the candidate targets as the position of the target.

13. The ultrasonic diagnostic apparatus according to claim 12, wherein the processing circuitry configured to superimpose the candidate targets on the second ultrasonic image generated through the second scanning comprises processing circuitry configured to superimpose the candidate targets at positions corresponding to positions of through holes for guiding a puncture needle in a puncture adaptor equipped in the ultrasonic probe.

14. The ultrasonic diagnostic apparatus according to claim 10, wherein
    the target comprises a puncture target, and
    the processing circuitry is configured to set the pivoting angle such that the scanning center which is the center of the region which is to be scanned by the first transducer set corresponds to a position of the puncture target based on the position of the puncture target.

15. An ultrasonic probe comprising:
    a first transducer set in which first transducers are arranged in a direction parallel to an axis of the ultrasonic probe;
    a second transducer set in which second transducers are arranged on a plane orthogonal to the axis; and
    a pivot shaft supporting the first transducer set and the second transducer set, and configured to pivot around the axis, wherein
    the second transducer set is configured to be slidable on and along the pivot shaft, and
    a pivoting radius of the second transducer set corresponds to a radius of curvature at which the second transducers of the second transducer set are arranged.

16. An ultrasonic diagnostic apparatus, comprising:
    an ultrasonic probe including a first transducer set in which first transducers are arranged in a direction parallel to an axis of the ultrasonic probe, a second transducer set in which second transducers are arranged on a plane orthogonal to the axis, a sensor for detecting a position, and a pivot shaft supporting the first transducer set and the second transducer set and configured to pivot around the axis, the second transducer set being configured to be slidable on and along the pivot shaft; and processing circuitry configured to:

perform a first scanning by the first transducer set to generate a first ultrasonic image and a second scanning by the second transducer set to generate a second ultrasonic image through the ultrasonic probe;

display at least the second ultrasonic image on a display;

calculate, when a region of the displayed second ultrasonic image generated through the second scanning is specified as a target, a target pivoting angle when a scanning plane of the first scanning includes the target based on the position of the target; and perform notification when a pivoting angle of the ultrasonic probe based on the detected position corresponds to the calculated target pivoting angle, wherein the second transducer set is configured to be movable along the direction parallel to the axis.

* * * * *